US008820546B2

(12) United States Patent
Moore

(10) Patent No.: US 8,820,546 B2
(45) Date of Patent: Sep. 2, 2014

(54) MOUNT FOR DENTAL CERAMIC BLOCKS

(75) Inventor: Paul Moore, Roscahill (IE)

(73) Assignee: Gate Dental Services Limited, Galway (IE)

( * ) Notice: Subject to any disclaimer, the term of this patent is extended or adjusted under 35 U.S.C. 154(b) by 390 days.

(21) Appl. No.: 13/122,088

(22) PCT Filed: Oct. 1, 2009

(86) PCT No.: PCT/EP2009/062789
§ 371 (c)(1),
(2), (4) Date: Aug. 25, 2011

(87) PCT Pub. No.: WO2010/037833
PCT Pub. Date: Apr. 8, 2010

(65) Prior Publication Data
US 2011/0297631 A1    Dec. 8, 2011

(30) Foreign Application Priority Data
Oct. 1, 2008 (IE) ................................ S2008/0792

(51) Int. Cl.
*A47F 7/00* (2006.01)
*A47F 5/08* (2006.01)
(Continued)

(52) U.S. Cl.
CPC .............. *A47F 5/0823* (2013.01); *A47F 7/0028* (2013.01); *B25H 3/003* (2013.01); *A61C 3/04* (2013.01); *A61C 1/14* (2013.01); *A61C 1/144* (2013.01)
USPC ........ 211/85.13; 211/69; 211/13.1; 211/60.1; 211/59.1

(58) Field of Classification Search
CPC ........... A47F 7/00; A47F 7/02; A47F 7/0028; A47F 7/0021; A47F 5/0823; A47F 5/0869; A47F 5/0815; A47F 5/08; A47F 5/0807; A47F 81/00; A47F 81/005; B65D 85/20; A61B 19/0256; A61B 19/0271; B25H 3/003; B25H 3/04; B25H 3/06; A61G 15/16; A61G 15/14; A61C 3/04; A61C 1/14; A61C 19/006; A61C 1/142; A61C 1/144; A61C 1/145

USPC ............... 211/57.1, 59.1, 70.6, 87.01, 85.13, 211/60.1, 69, 69.1, 69.5–69.9, 88.01, 89.01, 211/90.01, 13.1, 70.7; 248/220.31, 220.41, 248/220.42, 220.43, 221.12; 433/77, 163; 206/368, 369, 370, 379, 63.5, 563, 206/362, 438, 443, 562, 564

See application file for complete search history.

(56) References Cited

U.S. PATENT DOCUMENTS
1,816,694 A * 7/1931 Pope ............................ 248/239
(Continued)

FOREIGN PATENT DOCUMENTS
DE   1899042 U   8/1964
DE   7703231 U1  5/1977
DE   3541141 A1  5/1987

*Primary Examiner* — Jennifer E Novosad
(74) *Attorney, Agent, or Firm* — Tutunjian & Bitetto, P.C.

(57) ABSTRACT

The present invention is directed to a dental mount for receiving and retaining a plurality of different dental ceramic blocks used in dental restoration treatments, wherein the dental mount comprises a substantially flat front face having a plurality of dental ceramic block receiving holes located thereon; each of the dental ceramic block receiving holes being dimensioned to form a retaining fit with any one of the different dental ceramic blocks. The advantage of providing a dental mount with dedicated holes for retaining any one of the dental ceramic blocks is that the dental mount can be used to comparatively present all the different types of dental ceramic blocks next to one another in an organized and graded manner so that a dentist may make quick and accurate comparisons between the different types of dental ceramic blocks. Furthermore, the dentist can quickly assess their stock levels by glancing at the dental mount. A further advantage is that the dental ceramic blocks are securely held apart from one another on the dental mount and therefore cannot damage one another when they are moved or transported.

11 Claims, 11 Drawing Sheets

(51) Int. Cl.
  *A47F 1/04* (2006.01)
  *B25H 3/00* (2006.01)
  *A61C 3/04* (2006.01)
  *A61C 1/14* (2006.01)

(56) References Cited

U.S. PATENT DOCUMENTS

| | | | |
|---|---|---|---|
| 3,204,776 A * | 9/1965 | Brown et al. | 211/70.6 |
| 4,770,297 A * | 9/1988 | Chang | 206/379 |
| 4,951,827 A * | 8/1990 | Moransais | 211/59.1 |
| 5,080,232 A * | 1/1992 | Leoncavallo et al. | 206/446 |
| 5,579,929 A * | 12/1996 | Schwartz | 211/74 |
| 5,996,818 A * | 12/1999 | Boje et al. | 211/74 |
| 6,112,897 A * | 9/2000 | Hu | 206/377 |
| 6,199,706 B1 * | 3/2001 | Shea | 211/87.01 |
| 6,474,481 B1 * | 11/2002 | Liu | 211/69 |
| 6,481,584 B1 * | 11/2002 | Cantley | 211/87.01 |
| 6,789,714 B1 * | 9/2004 | Benson et al. | 224/584 |
| 6,796,440 B2 * | 9/2004 | Wang | 211/70.6 |
| 6,923,407 B2 * | 8/2005 | Takeuchi | 248/73 |
| 6,945,414 B1 * | 9/2005 | Stevens et al. | 211/94.01 |
| 7,424,958 B1 * | 9/2008 | Eley | 211/70.6 |
| 7,798,338 B2 * | 9/2010 | Maheu et al. | 211/94.02 |
| 7,845,501 B1 * | 12/2010 | Fosburg et al. | 211/103 |

* cited by examiner

MOUNT FOR DENTAL CERAMIC BLOCKS

INTRODUCTION

This invention relates to the dental industry. In particular, this invention relates to the storage and display of materials used in dental restoration techniques.

Dental restoration has become increasingly popular in recent times due to procedures becoming more affordable and due to the availability of high quality dental restoration from dentists in their own dental surgeries. Previously, dental restoration procedures were expensive and only available in larger, regional dental surgeries. However, this has changed in recent times and the widespread availability of the dental restoration procedures is in part due to new types of dental restoration techniques that have been developed to assist dentists in forming replacement tooth-pieces such as crowns, veneers, inlays, onlays, dentures, bridges, and the like. These new type of dental restoration techniques include Chairside Economical Restoration of Esthetic Ceramics (CEREC), or the E4D (TRADEMARK) system as developed by the D4D Technologies LLC.

CEREC and E4D are both dental restoration techniques which can be used to create a very accurate, precisely manufactured replacement tooth-piece from a piece of ceramic material which is inserted into a patient's mouth.

The first stage in the these methods is to map the tooth which requires the dental restoration work. The tooth is mapped digitally and consequently a virtual 3-D model of the missing portion of the tooth, which will eventually receive the replacement tooth-piece, is generated. This virtual 3-D model of the replacement tooth-piece is typically created using bespoke software. Data representing the virtual 3-D model of the replacement tooth-piece is then transmitted to a manufacturing machine. The manufacturing machine will mill the replacement tooth-piece from a block of ceramic, usually porcelain. The manufacturing machine very precisely and very accurately mills the dental ceramic block into the desired shape of the replacement tooth-piece in accordance with the specifications of the virtual 3-D model. It is essential that the milling of the ceramic block be carried out in an accurate manner, and consequently small manufacturing tolerances are enforced, so that the replacement tooth-piece fits comfortably into the patient's mouth.

In order to achieve the small manufacturing tolerances, a computer aided manufacturing (CAM) technique is used to control the manufacturing machine, typically known as Cad-Cam. In this manner, the virtual 3-D model of the replacement tooth-piece can be almost perfectly replicated as the movement of the milling bit in the manufacturing machine is controlled by a computer. Also, one of the primary advantages of using the CadCam technique is that the milling of the replacement tooth-piece can be carried out chairside in the dental surgery of the patient's dentist. No manufacturing skill or experience is required of the dentist as the computer aided manufacturing machine will produce the replacement tooth-piece in a semi automated fashion for the dentist without clinical input from the dentist related to the clinical situation. Therefore, the patient can receive their replacement restoration in a relatively short amount of time without having to await for a distant laboratory to fabricate the restoration.

The ceramic block that is used in the above-mentioned CadCam system, which is sometimes referred to as a "machined blank", is comprised of a piece of ceramic material that is mounted on an associated chuck. The chuck depends downwardly from the base of the piece of ceramic material and is used to hold the piece of ceramic material securely in place during machining by the computer aided manufacturing machine. Typically, the CadCam system will have a complimentary engaging mechanism to clamp to the chuck and fix the ceramic block securely in place in a desired location within the computer aided manufacturing machine, so that the very precise milling that is required can be achieved.

The main advantage of these CadCam system is that is allows the dentist to immediately produce the required replacement tooth-piece whilst the patient waits and can measure, produce, insert and fix the replacement tooth-piece in the patient's mouth in a matter of 1-2 hours. As a consequence, CEREC, E4D and other similar dental restoration techniques are becoming more popular. However, the speed and ease with which dentists may produce the replacement tooth-pieces presents some problems for the dentists and for the patients.

The choice of ceramic as the material to be used was made as ceramic, and particularly porcelain, bears a similar resemblance to teeth. However, as teeth vary in colouration and translucency from person to person, providers of the ceramic blocks for use in these dental restoration procedures must provide a wide range of ceramic blocks having different colours and translucencies, so that extremely close aesthetic matches can be established between the replacement tooth-piece, made from the ceramic block, and the tooth in the patient's mouth. Furthermore, the ceramic blocks must be provided in varying sizes as the ceramic blocks must be machined to fit small and large teeth, and it is preferable, for both economical and time-related reasons, that a minimum amount of machining is carried out chairside by the computer aided manufacturing machine.

As the process using CadCam systems is relatively quick and can be carried out almost immediately the dentist must immediately choose the size, colour and translucency of the ceramic block which their replacement dental tooth-piece will be machined from. In addition to the size, translucency and colouration variations, different manufacturers produce different ceramics with different physical properties, and all of these afford the dentist a wide range of possible ceramic blocks to choose from. As a result, dentists must stock a large range of different types of ceramic blocks having different qualities, colours, translucencies and sizes.

At present, dentists stock the large range of ceramic blocks in trays or drawers in their dental surgeries. Each drawer contains a number of compartments and each compartment is filled with a particular size, colour, translucency and quality of ceramic block. When the dentist has to choose which ceramic block most closely matches the patient's teeth, the dentist has to pull open the correct drawers and retrieve different samples for each of the different types of ceramic blocks from the different compartments within the drawers. Clearly, this is a cumbersome and time-consuming task for the dentist. Individually opening all of the drawers to take out different samples of ceramic blocks to compare to the patient and takes a long time and is also potentially frustrating for the dentist as they must remember which sample of ceramic block came from which compartment within which drawer. As many of the ceramic blocks look almost identical, it is very easy to replace one of the ceramic blocks into the wrong compartment in one of the drawers. Consequently, due to an error in replacing a ceramic block, a minimum number of ceramic blocks in a particular shade, colour, size, translucency and manufacturer type may appear to be available, but in fact are not. As a result, if the dentist does not notice this shortage in their stock control, the required number of ceramic blocks may not be available for a different procedure on a different patient.

Also, as previously mentioned above, the use of the CEREC dental restoration procedure requires that dentists stock a wide range of ceramic blocks so that almost immediate machining of the ceramic block may be carried out in order to produce the replacement tooth-piece for the patient during their current visit to the dental surgery. It is important that dentists have an accurate account of the stock levels for each type of ceramic block so that the required ceramic block is available to the patient. At present, as drawers are used to store the different types of ceramic blocks, it makes it very difficult for dentists to keep track of which ceramic blocks are sufficiently in stock and which types of ceramic blocks need to be re-ordered. In order to assess the stock levels for each type of ceramic block, the dentist must open each of the drawers and count the quantity of each type of ceramic block those than each compartment of every drawer. This is time-consuming and somewhat impractical if and very large range of ceramic blocks is stored by the dentist.

An alternative to manually checking the stock levels for each type of ceramic block is to use a dedicated stock level management system. Typically, these systems are computerised. The difficulty with using such bespoke stock level management systems is that they increase the administrative duties of the dentist as the data in the stock level management system must be continually updated. As before, this will be time-consuming for the dentist to implement. Furthermore, as a computer must be used there will be associated costs with the acquisition and maintenance of the computer hardware.

Lastly, an easy comparison between different types of ceramic blocks cannot be made by a dentist as the different ceramic blocks are currently stored in different compartments within different drawers. When the dentist retrieves some samples of the different types of ceramic blocks, the patient will be able to make a comparison, however, the comparison will only be based on a small set of ceramic blocks that the dentist can hold in their hand or place on a small chairside table. As the dentist must make a choice between an ever expanding amount of different types of ceramic blocks, it is difficult for both the dentist and patient to maintain a note of which types of ceramic blocks have already been seen and compared to other types of ceramic blocks.

Moreover, as the ceramic blocks are loosely stored, the act of carrying out the comparisons can quite easily become disorganised thus making it more difficult for the dentist to choose the correct ceramic block having the closest matching colour and translucency as their tooth.

It is a goal of the present invention to provide an apparatus that overcomes at least one of the above mentioned problems.

SUMMARY OF THE INVENTION

The present invention is directed to a dental mount for dental ceramic blocks that are used in dental restoration procedures, said dental ceramic blocks comprising a ceramic head attached to a chuck, the dental mount comprising a tabular body having a front face and a rear face and a plurality of dental ceramic block receiving holes in the front face of the tabular dental block, the dental ceramic block receiving holes being arranged in a preset pattern for retaining the dental ceramic blocks on the tabular body, spaced apart from one another, in a desired, organised and graded manner.

The advantage of providing a dental mount with dedicated dental ceramic block receiving holes for retaining dental ceramic blocks is that the dental mount can be used to comparatively present all the different types of dental ceramic blocks next to one another so that a dentist may make quick and accurate comparison between different types of dental ceramic blocks. The different types of dental ceramic blocks may be arranged according to the size, colour, translucency and/or quality. Having the full range of dental ceramic blocks immediately in front of them, a dentist, and in some cases a patient, will be able to make a better comparison between the different types of dental ceramic blocks available to them. This will greatly simplify the procedure and will allow a quicker, better comparison to be made. In particular, the preset pattern will allow the dentist to arrange the different types of ceramic blocks in a graded fashion depending on their size, colour, translucency and/or price to further simplify the comparison for the dentist.

Whilst it may be common to use mounts for displaying different objects next to one another, traditionally, dentists have always used compartments, typically within drawers, to store the different types of ceramic blocks, and indeed other dental equipment. The concept of using a dental mount, particularly one which can be used for comparison purposes in addition to storage purposes, has never been considered before in the dental profession due to tradition, as well as hygiene-related reasons. The concept of using a dental mount represents a radical departure from what is commonly found in dental surgeries today.

The dental mount itself, and indeed the benefits of the dental mount, may be considered to be of a relatively simple nature, however, the concept of using the dental mount in place of the widely available and commonly used drawers is not a simple choice to have made—it is contrary to tradition and contrary to common practice in many dental surgeries.

Furthermore, the use of a dental mount having a pre-set pattern of dental ceramic block receiving holes on the front face of the dental mount will allow the dentist to quickly assess the level of stock for each type of dental ceramic block by simply glancing at the dental mount. For example, if the dental mount comprises twenty rows of ten columns, and each row is used to stock a different type of dental ceramic block, then a quick analysis of the dental mount by the dentist would allow the dentist to assess their level of stock for each type of dental ceramic block by counting the number of empty holes on each row. This offers a very quick and easy solution to taking a stock check of the number of different types of dental ceramic blocks that the dentist has in their possession without the need for any complex stock level management systems.

A further advantage is that the dental ceramic blocks are securely held apart from one another and therefore cannot damage one another when the dental ceramic blocks are being transported. For example, the dentist may hang the dental mount from a wall for display purposes, and as needed, take down the dental mount from the wall and bring the mount chairside so that the patient and dentist may take a close-up a few of the different shades and colours of the various types of dental ceramic block. As the dental mount securely holds the various dental ceramic blocks and prevents them from hitting off one another, no damage will be done to any of the dental ceramic blocks as the dental mount is repeatedly hung on the wall and taken off to be brought chairside.

In a further embodiment, each dental ceramic block receiving hole is substantially cylindrical in shape to receive and retain the chuck of a dental ceramic block.

In a further embodiment, each dental ceramic block receiving hole comprises one or more inwardly extending protrusions on a side wall of the dental ceramic block receiving hole.

In a further embodiment, the protrusions are dimensioned to form a retaining fit with the chuck of the dental ceramic block. In addition to using the chuck for computer aided manufacturing purposes, it is advantageous to use this feature of the ceramic blocks to allow the dental ceramic blocks to the retained by the dental mount.

In a further embodiment, each dental ceramic block receiving hole comprises a bevelled rim.

In a further embodiment, the pre-set pattern of dental ceramic block receiving holes is divided into groups to form sets of dental ceramic block receiving holes on the front face of the dental mount. This will allow the dentist to organise the dental ceramic blocks according to colour size, manufacturer and other such differentiating factors.

In a further embodiment, the dental mount further comprises one or more means, for hanging the dental mount, on the rear face of the dental mount.

In a further embodiment, the dental mount further comprises a plurality of surface engaging legs on the rear face of the dental mount.

In a further embodiment, the dental mount further comprises a substantially planar front face.

In a further embodiment, the dental mount comprises one or more means for hanging the dental mount and/or a plurality of surface engaging legs located on the rear face of the dental mount, opposite the planar front face of the dental mount.

In a further embodiment, the means for hanging the dental mount comprise one or more keyhole slots.

In a further embodiment, the dental mount comprises a plurality of inter-locking sections that may be releasably engaged with each other to alter the size of the dental mount. This allows the dentist to use a large mount to show a patient all of the various types of ceramic blocks, but also allows the dentist to detach only a portion of the mount to bring chairside to discuss the types of ceramic blocks in greater detail with the patient.

In a further embodiment, the dental mount is constructed of medical grade latex with a polypropylene casing.

In a further embodiment, the dental mount is constructed of a cleanable and sterilisable material.

In a further embodiment, the dental mount is constructed of wood.

In a further embodiment, the dental mount further comprises bevelled edges.

In a further embodiment, the dental mount further comprises a transparent lid. The lid will help to keep the ceramic blocks clean and sterile for immediate use on a patient.

DETAILED DESCRIPTION OF EMBODIMENTS

The invention will be more clearly understood by the following description of some embodiments thereof, given by way of example only with reference to the accompanying drawings, in which.

Figure 1:
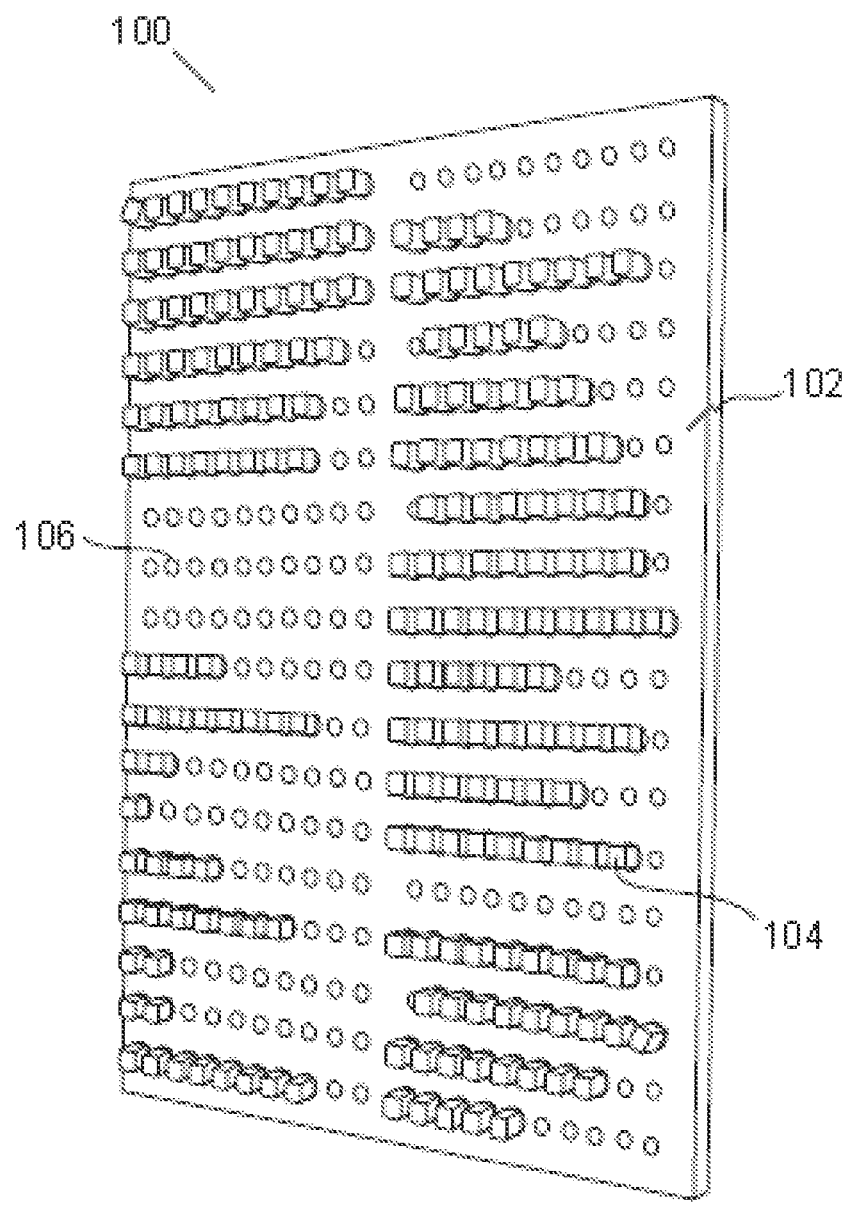
FIG. 1 is a perspective view of a dental mount retaining a plurality of dental ceramic blocks in accordance with the present invention.
Figure 2:
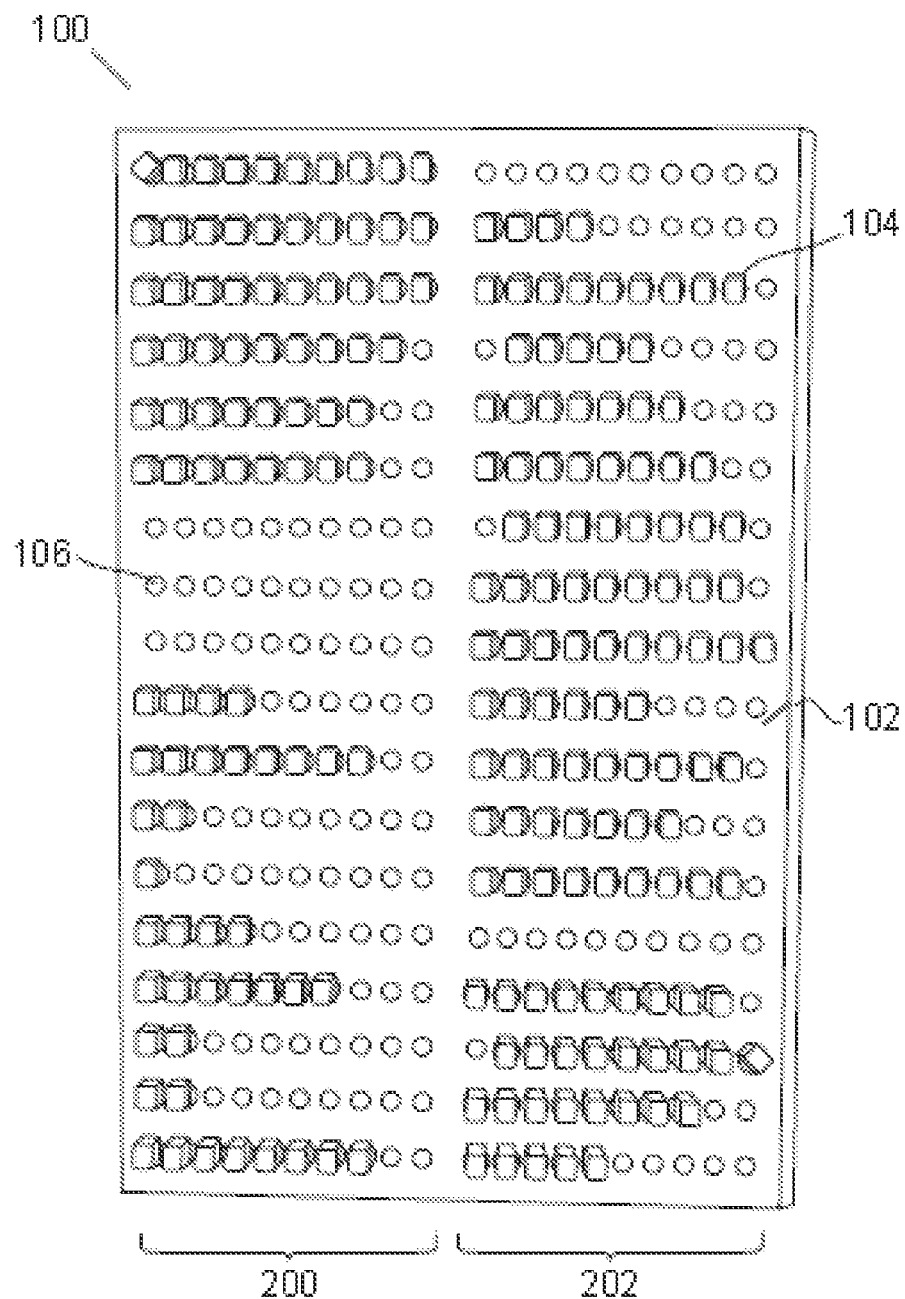
FIG. 2 is a front view of the dental mount of FIG. 1.
Figure 3:
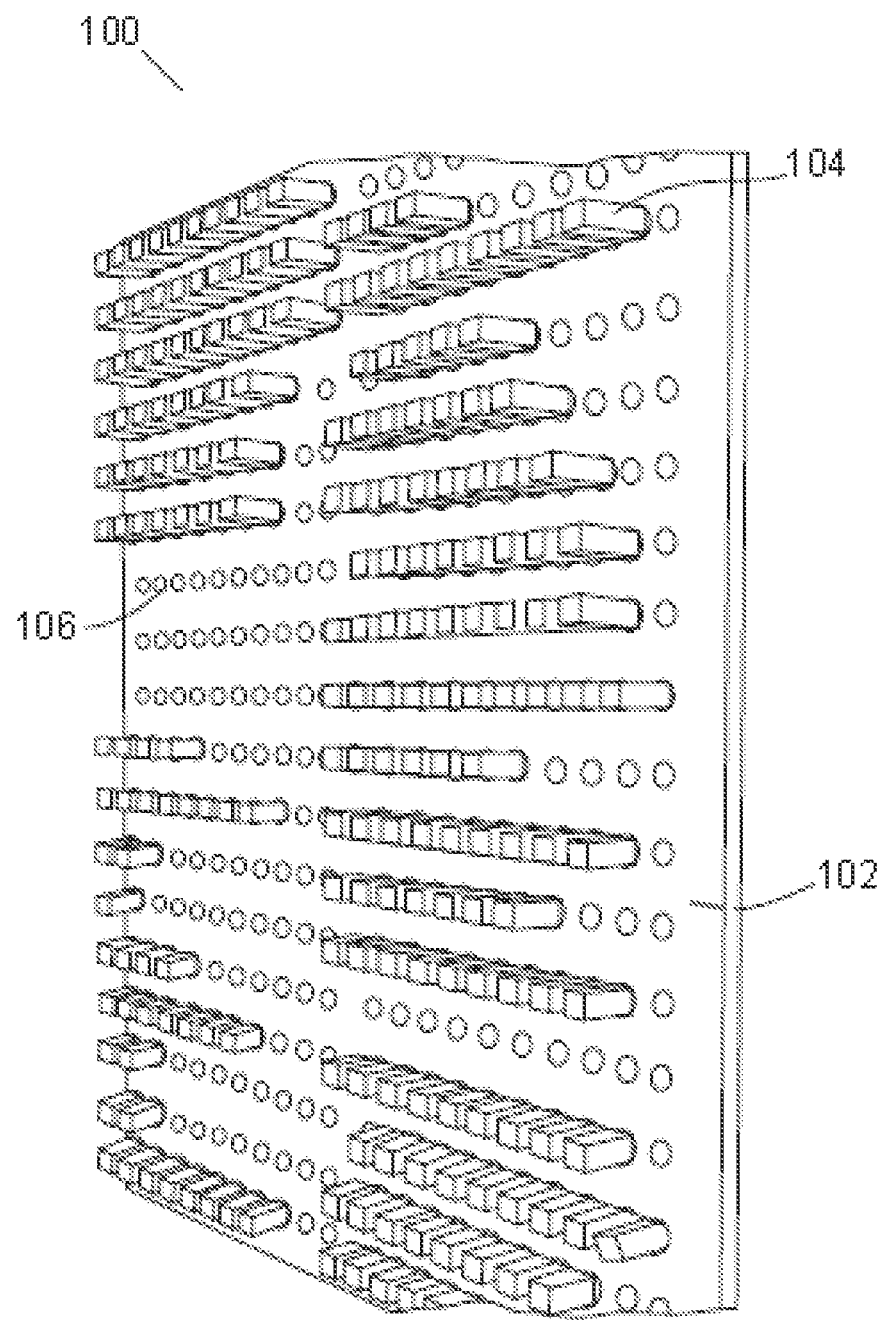
FIG. 3 is a detail perspective view of the dental mount of FIG. 1.
Figure 4:
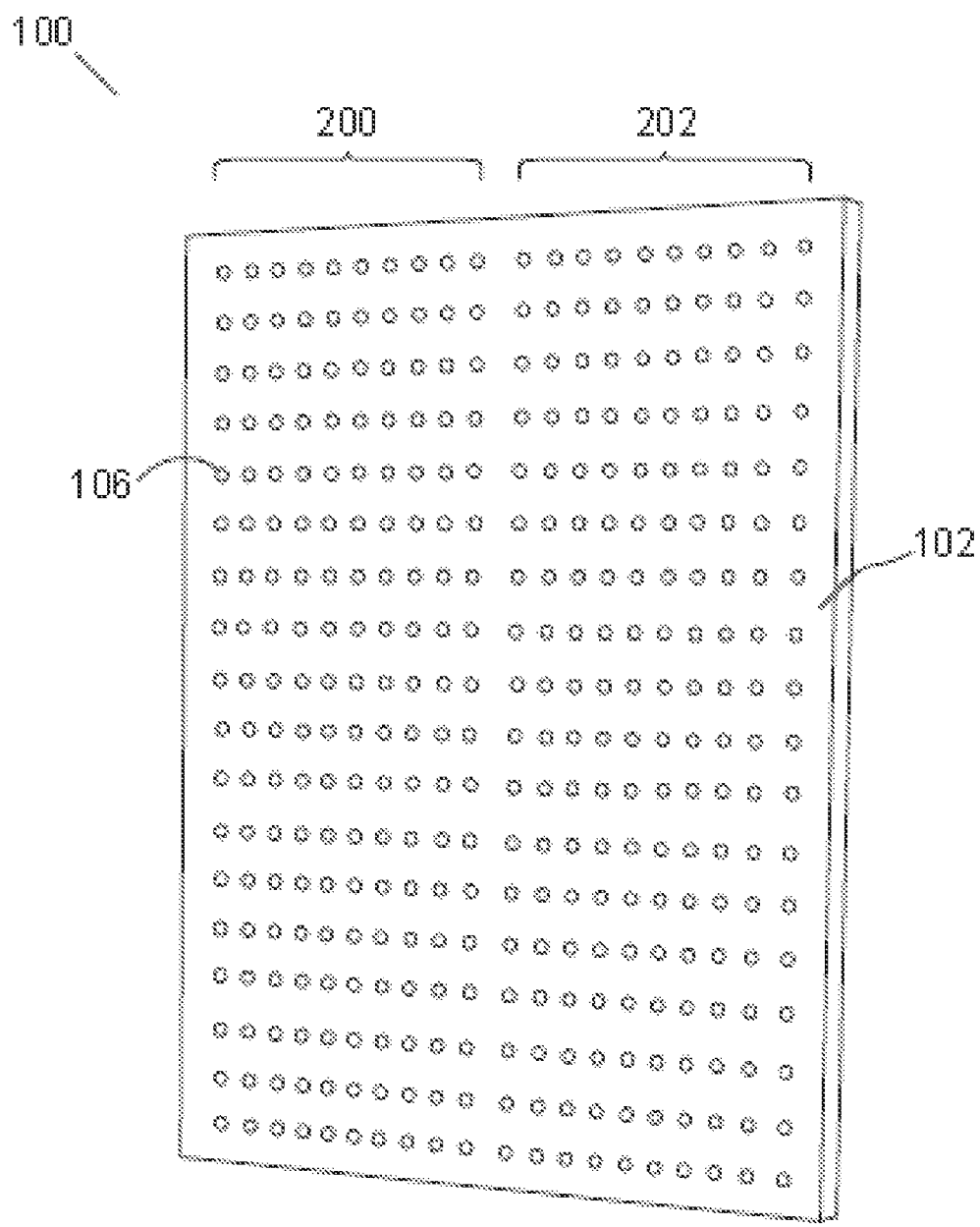
FIG. 4 is a front view of the dental mount of FIG. 1 without any dental ceramic blocks inserted into the plurality of receiving holes in the dental mount.

Referring to the drawings and initially to FIGS. 1 to 4 thereof, there is provided a dental mount indicated generally by the reference numeral 100. The dental mount 100 is substantially tabular, which is to say the mount is substantially flat having two relatively long, parallel sides that are orthogonal to two relatively short, parallel sides. The dental mount 100 comprises a front face 102 which has a plurality of receiving holes, that are through holes 106 bored into it. Each of the through holes 106 is dimensioned to receive and retain a dental ceramic block 104 respectively. The through holes 106 are substantially cylindrical in shape.

In this embodiment, the through holes 106 are arranged into two sets 200, 202 of ten columns and eighteen rows of through holes 106 respectively. In a further embodiment (not shown) the through holes 106 may be grouped into a preset pattern having differently sized sets or clusters to allow the dentist to group the plurality of dental ceramic blocks 104 into groups of dental ceramic blocks 104 having approximately the same size, colour, translucency, shade or manufacturer type.

Figure 5:
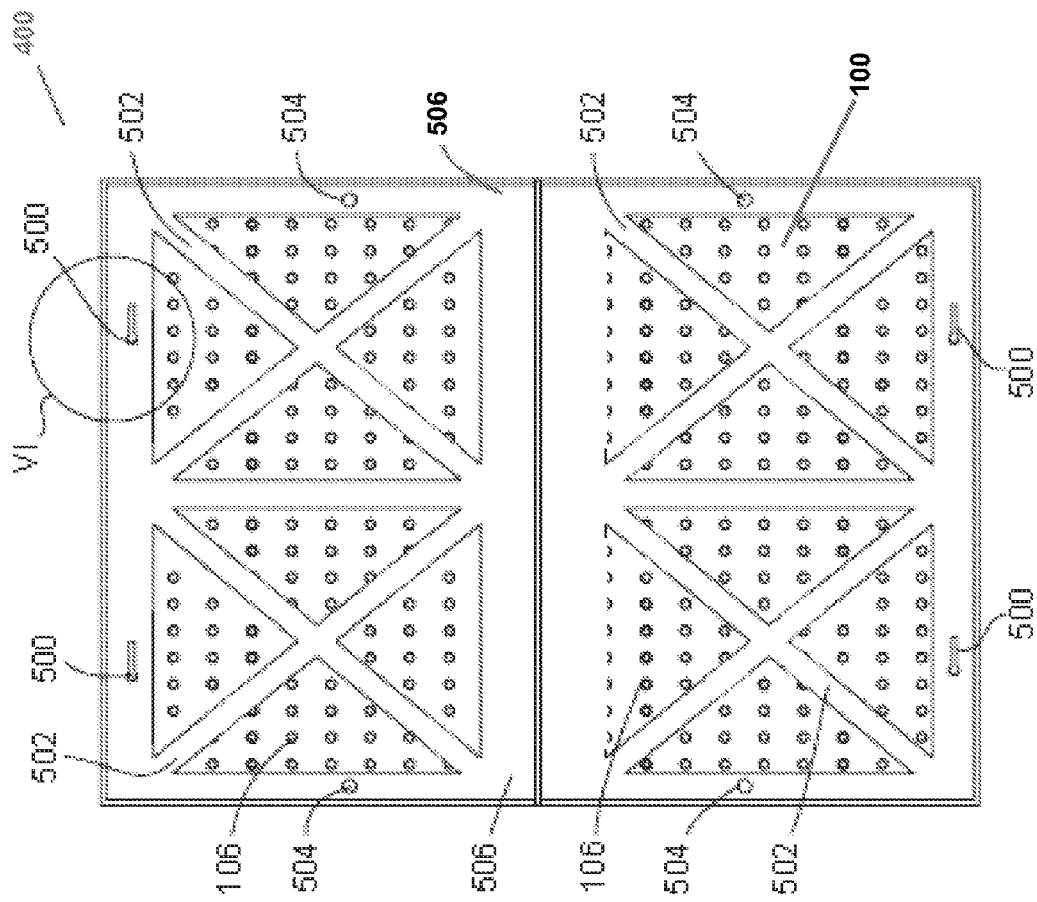
FIG. 5 is a rear view of a dental mount in accordance with a further embodiment of the present invention.

With reference to FIG. 5, wherein like parts previously described have been assigned the same reference numerals, there is provided an assembly 400 of mounts 100, the assembly having a back frame 506 that opposes a front face 102 of any of the mounts 100. The back face 506 comprises a plurality of criss-crossed supports 502 which support the frame 506 of the mount 100, and provide the mount 100 with some rigidity. One of the four mounts 100 may be removed from the assembly 400. A plurality keyhole slots 500 are provided on the outer portions of the back face 506 of the assembly 400. Furthermore, a plurality of surface engaging legs 504 abut to the back face 506 of the assembly 400. The back face 506 will become an underside face if the assembly 400 is placed in a horizontal position on a surface or countertop (not shown). The legs 504 may be adjustable in height relative to the back of the assembly 400 so as to present the assembly 400 at a tilted angle relative to the surface or countertop. The keyhole slots 500 or legs 504 may alternatively be fixed directly to one or more mounts 100.

Figure 6:
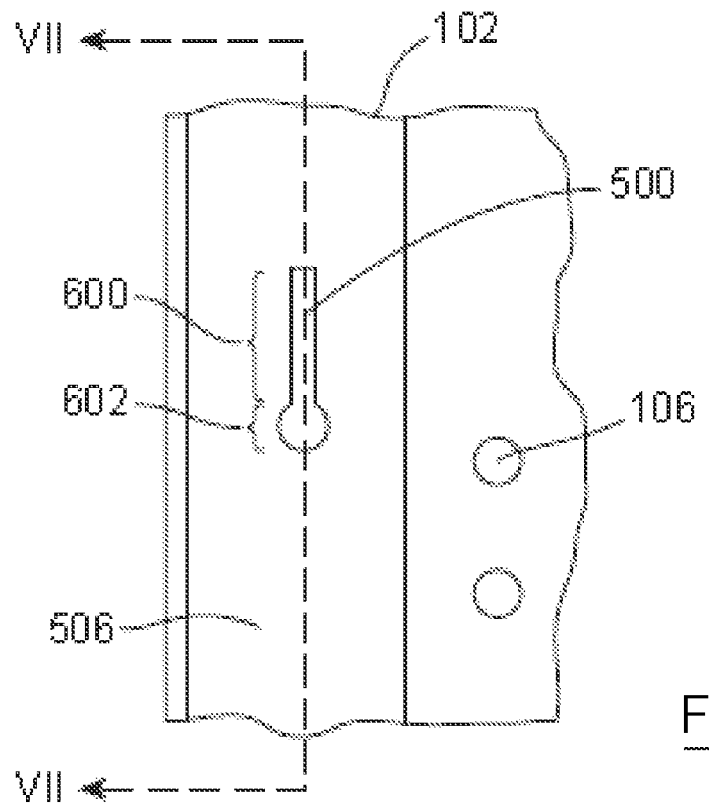
FIG. 6 is a detail view of an encircled portion of the dental mount of FIG. 5.
Figure 7:
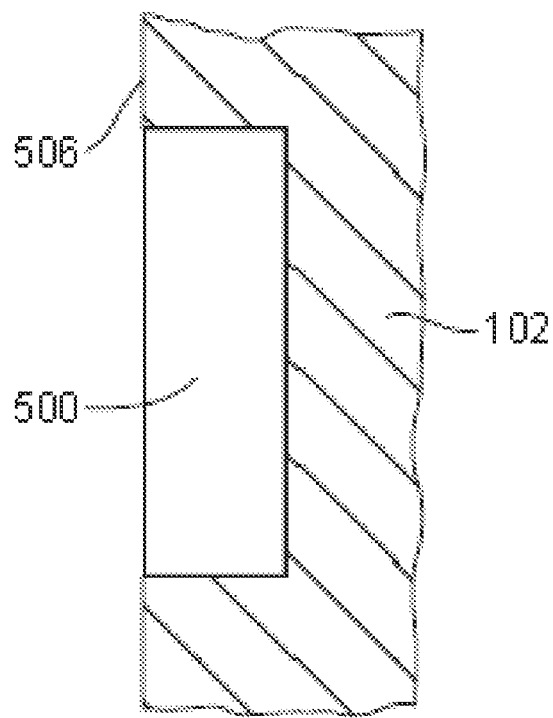
FIG. 7 is a cross-sectional view of a portion of the dental mount of FIG. 6 along line VII-VII.

Referring to FIGS. 6 and 7, the keyhole slot 500 comprises a bore 602 dimensioned to receive and release a head of a fixture such as a screw, nail or the like. An associated, coupled channel 600 is proportioned to have an opening width that is wide enough to allow a stem of the fixture to pass through, but narrow enough to prevent the head of the fixture from passing through. Thus, the head of a fixture such as a screw (not shown) may be passed through the bore 602 of the keyhole slot 500 and the mount 100 is then slid in the direction of the channel 600 to hang the mount 100 on the fixture (not shown). FIG. 7 shows a cross-section of the keyhole slot 500 along line VII-VII of FIG. 6.

Figure 8:
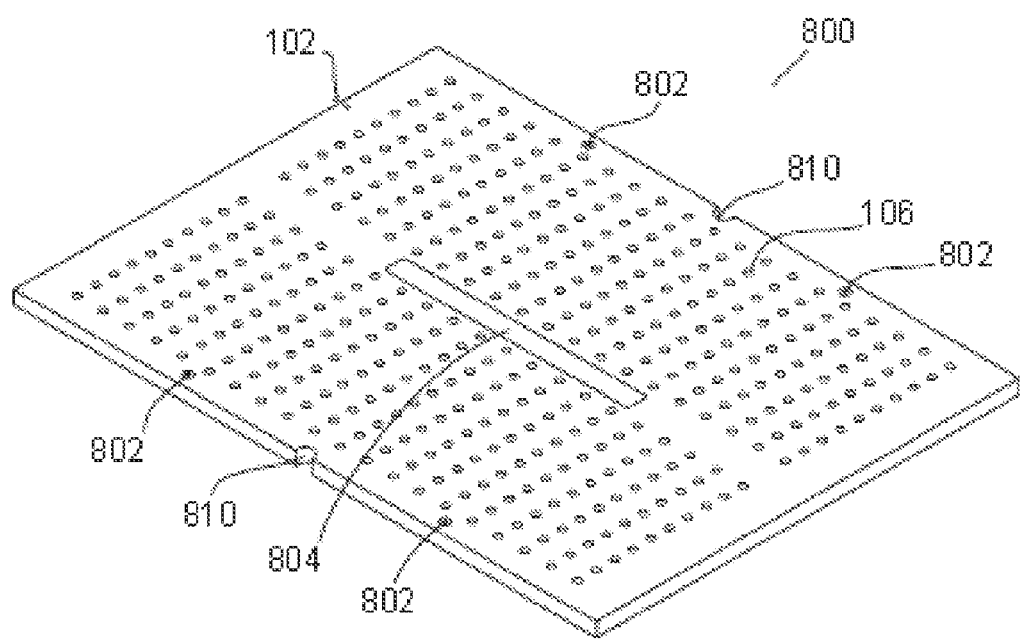
FIG. 8 is a perspective view of a dental mount in accordance with a further embodiment of the present invention.
Figure 9:
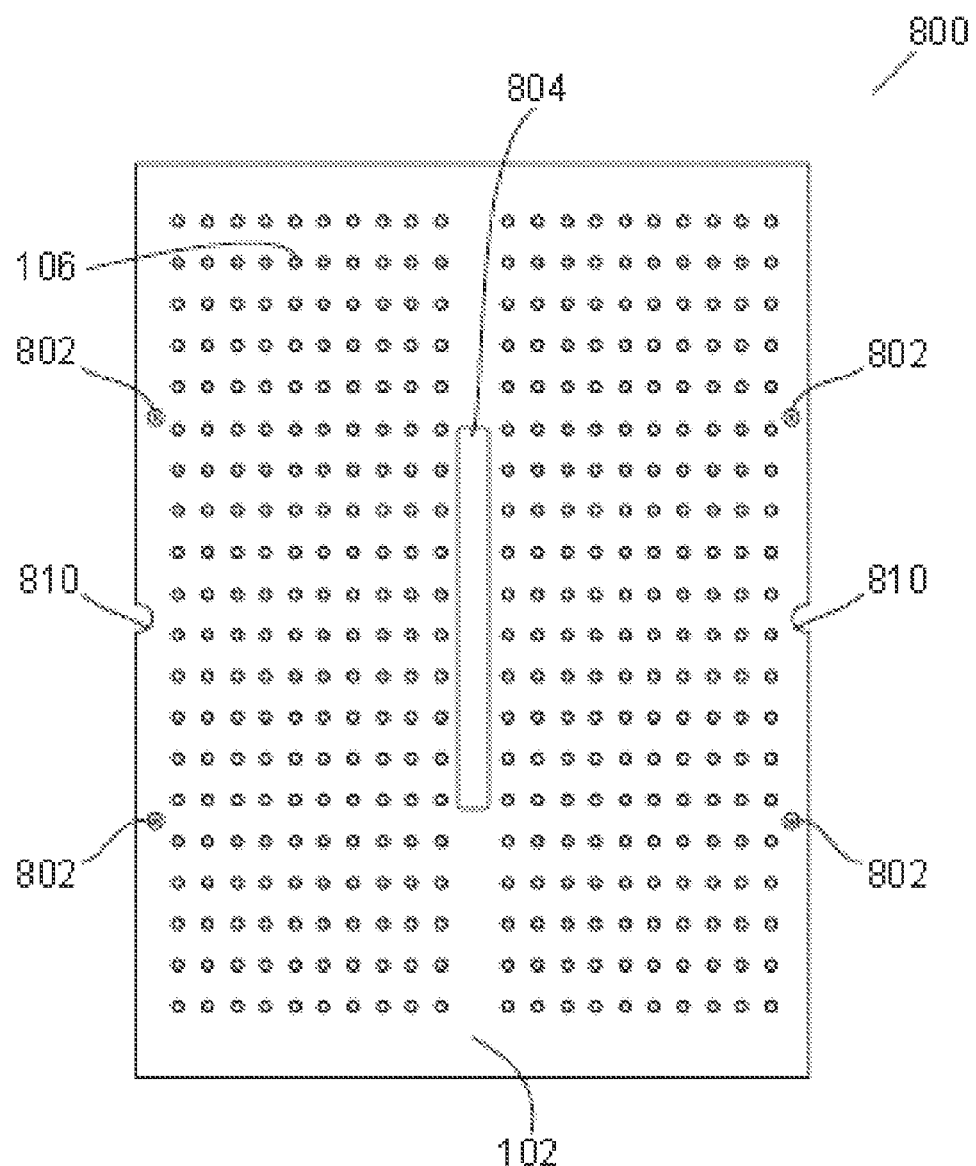
FIG. 9 is a front view of the dental mount of FIG. 8.
Figure 10:
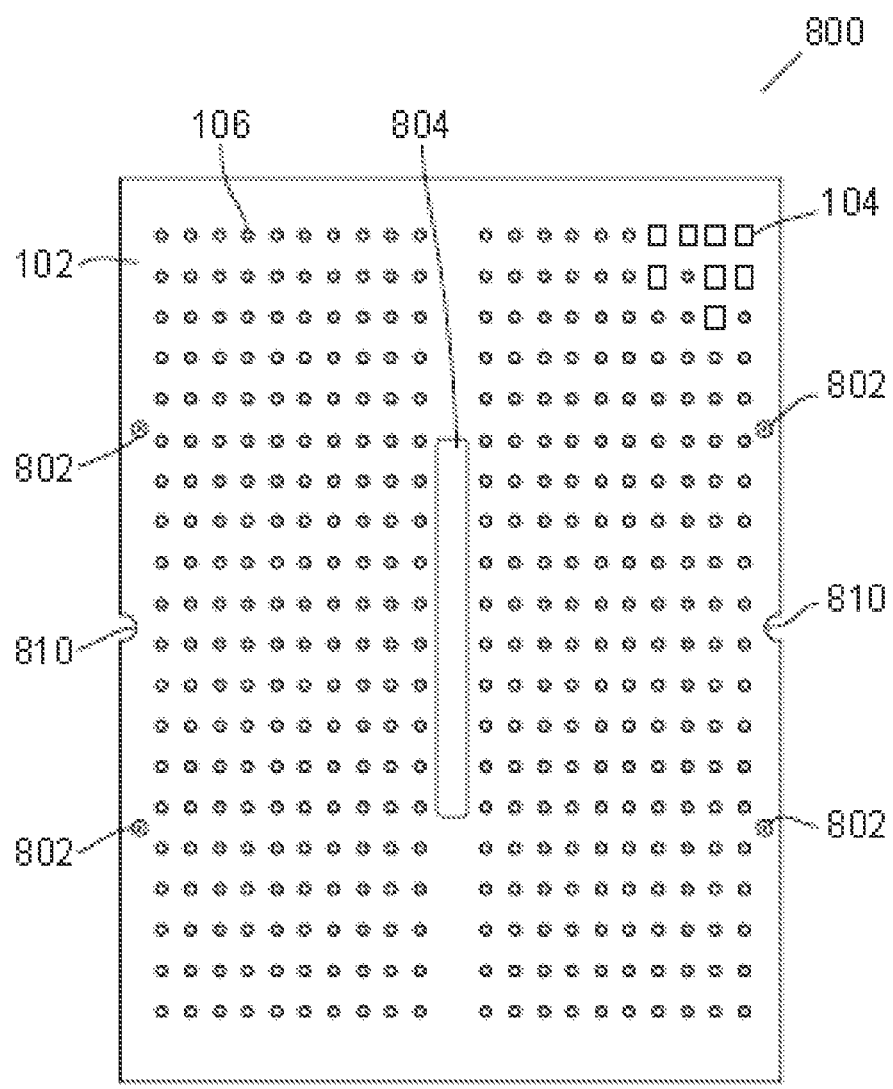
FIG. 10 is a front view of the dental mount of FIG. 8 with a plurality of dental ceramic blocks inserted into the plurality of receiving holes in the dental mount.

With reference to FIGS. 8 to 10, wherein like parts previously described have been assigned the same reference numerals, there is provided a mount indicated generally by the reference numeral 800. The mount 800 comprises a front face 102 as before. A plurality of through holes 106 are arranged in a pre-set, grid-like pattern on the mount 100. A plurality of dental ceramic blocks 104 may be stored in the through holes 106.

Pre-drilled connecting holes 802 are provided on the mount 800 to allow the mount to be fixedly secured to a wall by a number of screws (not shown) or other such fixture means. Screws, nails, bolts can be used to hang the mount 800 on a wall using the pre-drilled connecting holes 802.

Gripping grooves 810 are provided on longitudinal sides of the mount 800. The gripping grooves 810 make it easier for a user to pick up the mount 800, particularly when the mount 800 is lying on a horizontal surface such as a countertop.

A brand label, or product label receiving slot 804 is provided on the front display face 102 of the mount 800. In further embodiment, this product label receiving slot 804 may alternatively be used to receive labels indicating which type of dental ceramic block is stored in each of the rows and/or columns of the grid-like pattern of through holes 106 on the mount 800.

Figure 11:
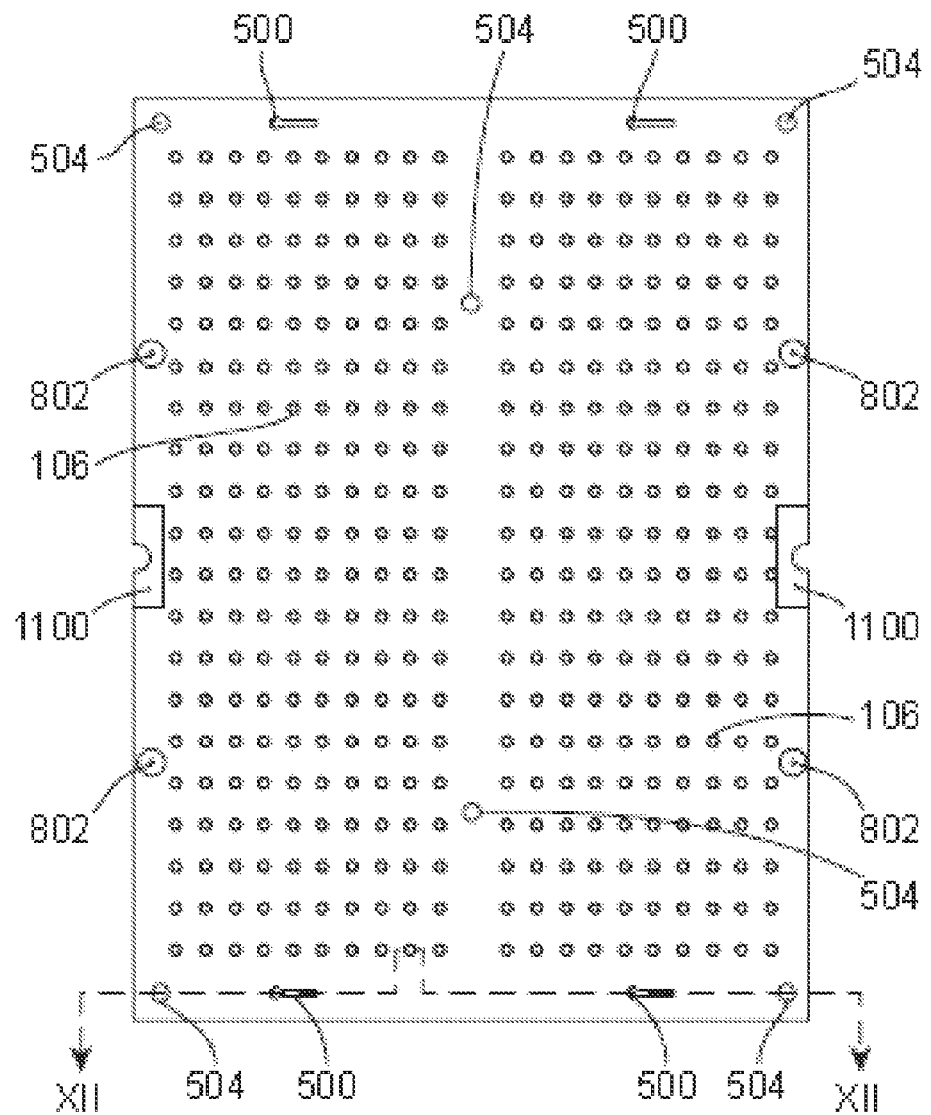
FIG. 11 is a rear view of the dental mount of FIG. 8.
Figure 12:
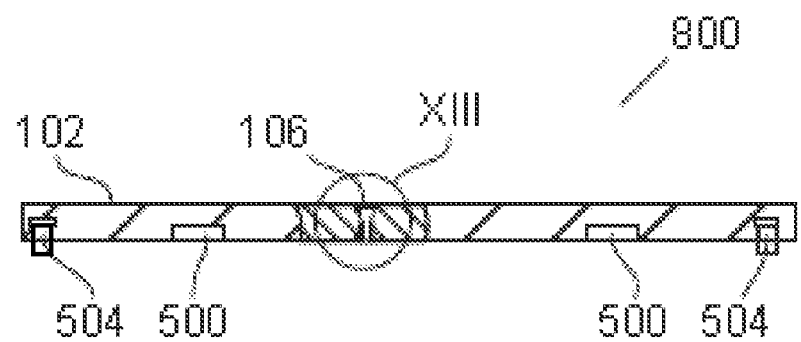
FIG. 12 is a bent cross-sectional view of the dental mount of FIG. 11 along line XII-XII.

Referring to FIGS. 11 and 12, wherein like parts previously described have been assigned the same reference numerals, there is provided the mount 800 comprising a plurality of through holes 106, a plurality of fixture engaging connectors 500 and a plurality of surface engaging legs 504. The rear side of the pre-drilled connecting holes 802 can be seen. Recesses 1100 are provided beneath the gripping grooves 810 to allow the mount 800 to be easily picked up by a user from a horizontal surface such as a countertop.

Figure 13:
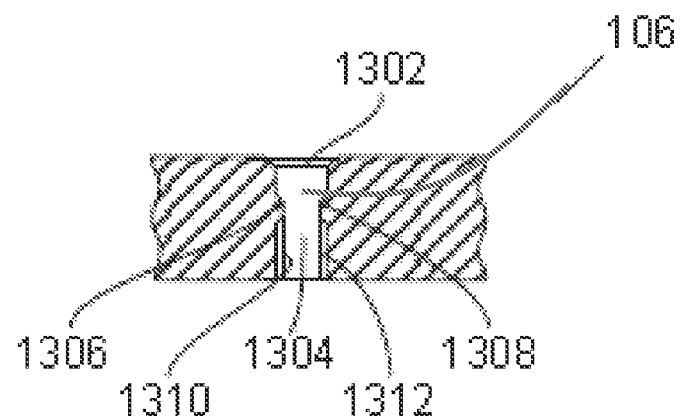
FIG. 13 is a detail view of an encircled portion of the cross-section of the dental mount of FIG. 12.

With reference to FIG. 13, wherein like parts previously described have been assigned the same reference numerals, a through hole 106 as a substantially cylindrical shape 1304. The upper edge of the through hole 106 comprises a bevelled rim 1302 to facilitate easy initial location of the chuck (not shown) within the through hole 106.

In this particular embodiment, the through hole 106 comprises a plurality of inwardly extending protrusions 1306, 1308. The inwardly extending protrusions 1306, 1308 are dimensioned to extend inwardly, radially into the through hole 106 so as to form a tight fit with a chuck (not shown) of a dental ceramic block (not shown). As the majority of chucks are of a standardised diameter, it is relatively easy to provide a through hole 106 which will positively retain dental ceramic blocks from a number of different manufacturers.

Further inwardly extending ribs 1310, 1312 are provided in the through hole 106. These protrusive ribs 1310, 1312 further assist with retaining a dental ceramic block in the through hole 106. It is envisaged that various types of protrusions or internal ribs may be used in order to assist with retaining the dental ceramic blocks in the plurality of through holes 106 in the mount 800.

The mount 100, 800 is constructed of an autoclavable material so that the mount 100, 800 may be cleaned to a regulated hygienic level. Furthermore, the use of through holes 106 assists with cleansing the mount 100, 800 to the regulated, hygienic level as bacteria cannot collect in the bottom of the holes as would occur with non-through holes.

It is envisaged that the mount 100, 800 will facilitate the labelling of various sets of through holes, rows of through holes, columns of through holes and the like so that a dentist may label which portions of the mount 100, 800 is being used to store various different types of dental ceramic blocks. The labelling may be achieved by providing a plurality of smaller rectangular plastic envelopes to receive rectangular pieces of cardboard having a particular label written on them. Such label receiving pouches are well known from various different fields.

In a further embodiment (not shown), the mount 100, 800 may further comprise a stand to allow a dentist to sit the mount 100, 800 on a countertop in a tilted manner so as to allow a patient to view the different dental ceramic blocks 104 at a convenient viewing angle.

It will be understood that the mount 100, 800 has been described comprising through holes to receive and retain each of the chucks on the dental ceramic blocks. In a further embodiment (not shown), it is envisaged that the mount may comprise non-through holes to receive a sufficient portion of the chuck to allow the dental ceramic blocks to be received and positively retained by the non-through hole in the mount. That is to say, the holes are simply bores, or blind holes in the front display face and do not penetrate through to the back face of the dental mount.

Throughout the following specification, the term "ceramic" shall be understood to encompass any type of non-metallic, synthetic material formed by heating. Furthermore, the term "dental ceramic block" will be understood to refer to blocks of ceramic which are used in the CEREC procedure or other similar procedures.

In the specification the term "comprise" or any grammatical variation thereof and the term "include" or any grammatical variation thereof are considered to be interchangeable and should be afforded the widest possible interpretation.

The invention is not limited to the embodiments hereinbefore described which may be varied in both construction and detail within the scope of the appended claims.

The invention claimed is:

1. A dental mount capable of retaining dental ceramic blocks that are used in dental restoration procedures, the dental mount comprising:
   a tabular body having a substantially planar front face and a rear face, being constructed of an autoclavable material so as to be cleanable and sterilizable; and
   a plurality of dental ceramic block receiving holes in the front face of the tabular body and being arranged in a preset pattern for retaining the dental ceramic blocks on the tabular body, spaced apart from one another, in a desired, organized and graded manner when chucks of the dental ceramic blocks are inserted into the receiving holes;
   wherein each of the dental ceramic block receiving holes comprises:
      a substantially cylindrical shape configured to receive and retain the chuck of the dental ceramic block;
      one or more inwardly extending protrusions on a side wall of the receiving hole and which are dimensioned to form a retaining fit with the chuck when inserted into the receiving hole;
      one or more inwardly extending ribs on a sidewall of the dental ceramic block receiving hole which are dimensioned to form a retaining fit with the chuck of the dental ceramic block, when the chuck of the dental ceramic block is inserted into the dental ceramic block receiving hole; and
      a beveled rim.

2. The dental mount as claimed in claim 1, wherein, the pre-set pattern of dental ceramic block receiving holes is divided into groups to form sets of dental ceramic block receiving holes on the front face of the dental mount.

3. The dental mount as claimed in claim 1, wherein, the dental mount further comprises one or more means, for hanging the dental mount, on the rear face of the dental mount.

4. The dental mount as claimed in claim 3, wherein, the means for hanging the dental mount comprise one or more keyhole slots.

5. The dental mount as claimed in claim 1, wherein, the dental mount further comprises a plurality of surface engaging legs on the rear face of the dental mount.

6. The dental mount as claimed in claim 1, wherein, the dental mount comprises one or more means for hanging the dental mount and a plurality of surface engaging legs located on the rear face of the dental mount, opposite the planar front face of the dental mount.

7. The dental mount as claimed in claim 6, wherein, the means for hanging the dental mount comprise one or more keyhole slots.

8. The dental mount as claimed in claim 1, wherein, the dental mount comprises a plurality of inter-locking sections that may be releasably engaged with each other to alter the size of the dental mount.

9. The dental mount as claimed in claim 1, wherein, the dental mount is constructed of medical grade latex with a polypropylene casing.

10. The dental mount as claimed in claim 1, wherein, the dental mount further comprises bevelled edges.

11. The dental mount as claimed in claim 1, wherein, the dental mount further comprises a transparent lid.

* * * * *